(12) United States Patent
Sklar

(10) Patent No.: US 6,612,310 B2
(45) Date of Patent: Sep. 2, 2003

(54) WINDOWED MEDICAL DRAPE

(75) Inventor: Martin Sklar, Needham, MA (US)

(73) Assignee: OEC Medical Systems, Inc., Salt Lake City, UT (US)

( * ) Notice: Subject to any disclaimer, the term of this patent is extended or adjusted under 35 U.S.C. 154(b) by 0 days.

(21) Appl. No.: 09/888,113

(22) Filed: Jun. 22, 2001

(65) Prior Publication Data

US 2002/0069882 A1 Jun. 13, 2002

Related U.S. Application Data

(60) Provisional application No. 60/213,320, filed on Jun. 22, 2000.

(51) Int. Cl.$^7$ .............................................. A61B 19/00
(52) U.S. Cl. ...................................... 128/849; 128/853
(58) Field of Search ................................ 128/849–856; 355/230, 231

(56) References Cited

U.S. PATENT DOCUMENTS

| | | | |
|---|---|---|---|
| 4,905,710 A | | 3/1990 | Jones |
| 5,429,142 A | * | 7/1995 | Szabo ........................ 128/853 |
| 5,433,221 A | * | 7/1995 | Adair ......................... 128/853 |
| 5,490,524 A | * | 2/1996 | Williams et al. ............. 128/849 |
| 5,732,712 A | * | 3/1998 | Adair ......................... 128/849 |

* cited by examiner

*Primary Examiner*—Michael A. Brown
(74) *Attorney, Agent, or Firm*—McAndrews, Held & Malloy, Ltd.; Peter J. Vogel; Michael A. Dellapenna

(57) ABSTRACT

An operating room drape for allowing the presence of a monitor or display panel close to a surgical field while maintaining a sterile field between the monitor and the surgical site. A window in the drape, or all of the drape, is formed of a high clarity material and at least the window is adapted to lie against the monitor screen to provide enhanced visibility. The window may be configured as a separate rectangular insert formed, for example, of a five mil EPV vinyl or other clear polymer medically acceptable material, and sterilized by a process such as ethylene oxide or gamma ray sterilization. The window material may be treated by a process such as corona discharge treatment to enhance its surface adherence properties, while a major portion of the drape, or a release portion, may be non-adherent to facilitate positioning of the window and also removal of the drape following use. The drape itself may constitute a bag.

15 Claims, 2 Drawing Sheets

WINDOWED MEDICAL DRAPE

CROSS-REFERENCE TO RELATED APPLICATIONS

This application is related to and claims the priority of U.S. Provisional Patent Application Ser. No. 60/213,320, filed on Jun. 22, 2000.

STATEMENT REGARDING FEDERALLY SPONSORED RESEARCH

Not Applicable.

BACKGROUND OF THE INVENTION

The present invention relates to surgery and it particularly relates to the maintenance of a sterile field in the vicinity of a surgical procedure.

In many surgical procedures, fluoroscopes, endoscopes, monitoring instrumentation or other devices are required, which employ video monitors or similar display screens to display images, messages or results which aid in the surgical procedure. Often the monitor is placed close to the surgeon, in or near the sterile field. However, monitors are generally not sterilizable, so a sterile drape must then be placed over the monitor to isolate it from the sterile field. General practice is to use a commonly available or generic operating room sterile drape for this purpose. However, such drapes, although of thin polymer material, are not highly transparent and may cause the display image to become distorted or poorly visible. Such draping also impedes access to the monitor in the event that adjustment, or user entry of information in the case of a touch screen display, becomes necessary.

Accordingly, it would be desirable to provide a more effective drape.

It would further be desirable to provide a monitor drape having at least a portion of high transparency.

It would further be desirable to provide a monitor drape that closely fits the monitor.

It would also be desirable to provide a sterile monitor drape having at least a region of high clarity that lies flat on a monitor screen and is effectively transparent to both light and touch.

SUMMARY OF THE INVENTION

One or more of these and other desirable ends are achieved in accordance with the present invention by the provision of an operating room drape having a window sized to fit a display screen of a monitor, and a draping body extending about the window for covering and isolating the monitor. The window is formed of a high transparency polymer, and is preferably of a thickness that allows transmission of tactile pressure, enabling touch-screen data entry through the drape. The draping body may be formed of a polymer bag, with the window secured in a cut-out region. The window may be treated with anti-glare material to assure visibility of the underlying screen. It may be formed of an electret material, i.e., one having immobilized static charge carriers, or otherwise treated such that it adheres flat to the display screen.

BRIEF DESCRIPTION OF DRAWINGS

These and other features of the invention will be understood from the following description and claims, taken together with illustrative figures of an embodiment thereof, wherein:

DETAILED DESCRIPTION OF THE INVENTION

The present invention is an operating room equipment drape for allowing the presence of a piece of equipment, such as a monitor, close to a surgical site while maintaining a sterile field between the equipment and the surgical site.

Figure 1:
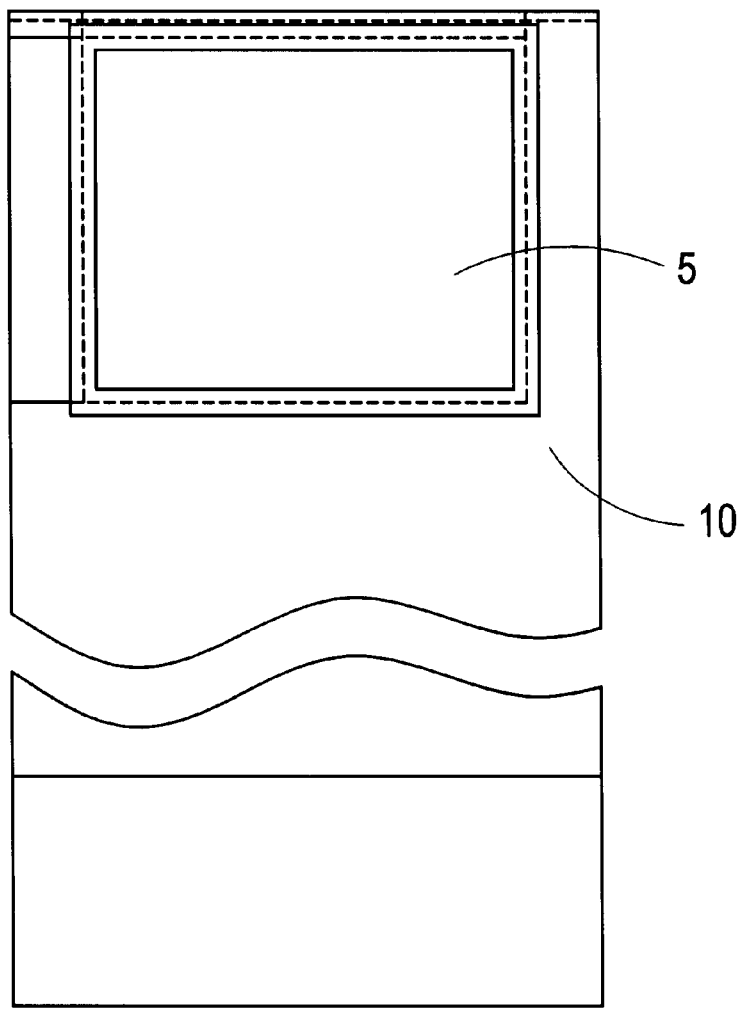
FIG. 1 shows one embodiment of a windowed medical drape in accordance with the preset invention.

One embodiment 10 is shown in FIG. 1. A window 5 in the drape 10, or all of the drape 10, is formed of a high clarity material and is adapted to lie against a monitor or display screen to provide enhanced visibility, while the body of the drape covers the device to maintain a sterile field. The window may be configured as a separate rectangular insert or cover sheet, formed, for example, of a five mil EPV vinyl or other clear polymer certified for such medical uses, or sterilized by a suitable, certifiable process such as ethylene oxide or radiation sterilization. The window material may be treated by a process such as corona discharge treatment to enhance its surface adherence properties. For example, one such mechanism creates an electret surface in which immobilized charge causes the polymer to adhere or cling to a smooth surface with which it comes in contact. The drape itself may constitute a large rectangular polymer bag, which may for example have a dimension of about two by about five feet, with the window placed in one large face of the bag at a position sufficiently offset from the closed end of the bag to be positionable in front of the screen of a typical monitor or flat panel display. Advantageously, the bag-shaped embodiment allows the drape to entirely or substantially entirely enclose the piece of draped equipment. However, it is also contemplated that the equipment may generally also have cables or connectors that extend out of the draped region. Since these are generally at a distal region and are not touched or manipulated by the surgeon, this does not impair the effectiveness of the drape. The bag may also have a tubular extension, such as a hose, that may be connected to a wall suction fitting or vent to assure adequate air circulation into and through the draped equipment for circuit cooling purposes.

For operating room use, the bag is simply placed over the monitor, and the surgeon gently presses the window against the screen so that it lies flat, adheres and maintains its position.

The contact surface of the window may be treated to enhance adherence. This may be done by corona discharge treatment in a manner to create a highly insulating surface with immobilized charge elements (e.g., electrets) at the surface. Alternatively, the window surface may be of a material, or have a treatment, that results in a surface energy or a surface material softness that promotes sticking contact. Instead of corona discharge treatment, a chemical coating may be used on the inner surface of the window facing the monitor, to assure that the window sticks flat to the display screen without the use of adhesives.

The non-windowed parts of the drape may be formed of a plastic having a non-adhering property, or all or a portion of its area may be treated to be non-clinging. These two surface properties in the window and non-window regions simplify the placement and alignment of the drape, and facilitate its subsequent removal after use. A coating may also be used to reduce glare. This may be applied to the inner surface that contacts the monitor so as to reduce internal reflection, and/or to enhance optical coupling of the window to the display screen.

The window portion of the drape may be thicker than the material of a typical surgical drape, i.e., thicker than several mils, but is preferably thin enough to allow manipulation and conforming fitting to the monitor screen, and in a preferred embodiment is sufficiently pliable to locally transmit mechanical pressure when touched. A thickness of five mils is considered suitable to reliably transmit the monitor image with extreme clarity and permit touch screen use of the monitor while maintaining a sterile field for the surgeon.

The window may be configured as a separate rectangular insert formed, for example, of a five mil EPV vinyl or other clear polymer medically acceptable material, and sterilized by a process such as ethylene oxide or gamma ray sterilization.

Figure 2:
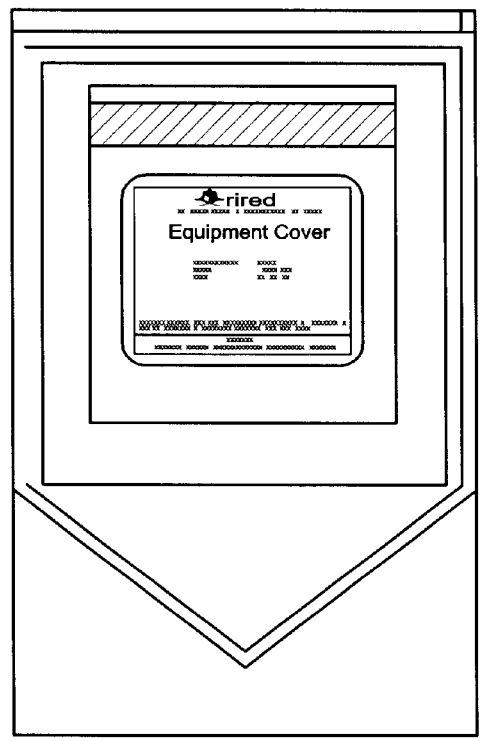
FIG. 2 illustrates the drape of FIG. 1 packaged before use.

Applicant contemplates that the sterile windowed drape of the present invention may be sterilized by conventional sterilization techniques, and may be packaged in a conventional medical bubble pack, as shown in FIG. 2. The drape may also be anti-static treated, and may be conventionally formed of a material such as polyethylene; or it may be formed of the same material as the window itself. Preferably, the window is a separate and different material from the rest of the drape so that it has a higher degree of dimensional stability and mechanical strength compared to the drape, while allowing the major body of the drape to be quite thin and loose.

FIGS. 1 and 2 illustrate a schematic plan view of one embodiment in which a clear monitor window is attached to cover an opening in one face of bag embodiment, and is secured by thermal sealing (i.e., fusing together of the window perimeter and the bag) about its periphery to form the closed draping assembly. FIG. 2 illustrates a plan view of the sterilized drape in a bubble pack container.

The invention being thus disclosed and illustrative embodiments described, further variations and modifications of the invention will occur to those skilled in the art, and all such variations and modifications are considered to be within the scope of the invention, as defined by the claims appended hereto and equivalents thereof.

What is claimed is:

1. A surgical drape, comprising:
   a sterile draping body; and
   a window in said body positioned to cover the face of a monitor when said body is draped over the monitor and to provide clear viewing thereof, said window being formed from a thin layer of a sufficiently pliable polymer material to enable the transmission of tactile pressure therethrough, wherein said window is formed of said polymer material having a thickness greater than a thickness of a material forming said body;
   wherein said body and window constitute a barrier for draping over equipment in an operating room to maintain a sterile field.

2. The surgical drape of claim 1, wherein said window includes material of high transparency adapted to adhere to the face of the monitor.

3. The surgical drape of claim 1, wherein said window is an anti-glare window.

4. The surgical drape of claim 1, wherein said window is coated on an interior side to enhance at least one of adherence and optical coupling of the window to the monitor.

5. The surgical drape of claim 1, wherein said body is formed of the same material as said window.

6. The surgical drape of claim 1, wherein said window is configured to maintain flatness and contact with the face of the monitor.

7. The surgical drape of claim 1, formed as a bag having said window in a major face thereof.

8. The surgical drape of claim 1, wherein the body includes a tubular extension located remotely from said window.

9. The surgical drape of claim 1, wherein said body is non-adherent and said window is adherent.

10. The surgical drape of claim 1, wherein said thin layer of polymer material forming said window is treated on at least one side thereof to form substantially permanent charge pairs.

11. The surgical drape of claim 1, wherein said window is formed from EPV vinyl.

12. The surgical drape of claim 1, wherein said window has a thickness of about 5 mils.

13. A surgical drape, comprising:
   a sterile draping body; and
   a window in said body positioned to cover the face of a monitor when said body is draped over the monitor and to provide clear viewing thereat said window being formed from a thin layer of a sufficiently pliable polymer material to enable the transmission of tactile pressure therethrough, wherein said thin layer of polymer material forming said window is treated on at least one side thereof to form substantially charge pairs;
   wherein said body and window constitute a barrier for draping over equipment in an operating room to maintain a sterile field.

14. A surgical drape, comprising:
   a sterile draping body; and
   a window in said body positioned to cover the face of a monitor when said body is draped over the monitor and to provide clear viewing thereof, said window being formed from a thin layer of a sufficiently pliable EVP vinyl polymer material to enable the transmission of tactile pressure therethrough;
   wherein said body and window constitute a barrier for draping over equipment in an operating room to maintain a sterile field.

15. A surgical drape, comprising;
   a sterile draping body; and
   a window in said body positioned to cover the face of a monitor when said body is draped over the monitor and to provide clear viewing thereof said window being formed from a thin layer of about 5 mils of a sufficiently pliable polymer material to enable the transmission of tactile pressure therethrough,
   wherein said body and window constitute a barrier for draping over equipment in an operating roam to maintain a sterile field.

* * * * *